(12) United States Patent
Geng

(10) Patent No.: US 7,939,497 B2
(45) Date of Patent: May 10, 2011

(54) DETECTION AND MODULATION OF SLIT AND ROUNDABOUT (ROBO) MEDIATED ANGIOGENESIS AND USES THEREOF

(75) Inventor: Jian-Guo Geng, Portage, MI (US)

(73) Assignee: Shanghai Institutes for Biological Sciences, CAS, Shanghai (CN)

( * ) Notice: Subject to any disclaimer, the term of this patent is extended or adjusted under 35 U.S.C. 154(b) by 0 days.

(21) Appl. No.: 10/386,386

(22) Filed: Mar. 10, 2003

(65) Prior Publication Data

US 2003/0236210 A1    Dec. 25, 2003

Related U.S. Application Data

(60) Provisional application No. 60/362,485, filed on Mar. 8, 2002.

(51) Int. Cl.
*A61K 38/16* (2006.01)
*A61K 39/395* (2006.01)
*C07K 14/00* (2006.01)

(52) U.S. Cl. ..... 514/13.3; 514/7.6; 514/19.3; 424/130.1; 424/133.1; 424/141.1; 424/143.1; 424/145.1; 530/350

(58) Field of Classification Search ....... 514/2; 530/350
See application file for complete search history.

(56) References Cited

U.S. PATENT DOCUMENTS

| | | | | |
|---|---|---|---|---|
| 5,593,990 | A | 1/1997 | D'Amato | 514/235.2 |
| 5,629,327 | A | 5/1997 | D'Amato | 514/323 |
| 5,686,102 | A | 11/1997 | Gross et al. | 424/450 |
| 5,693,762 | A * | 12/1997 | Queen et al. | 530/387.3 |
| 5,712,291 | A | 1/1998 | D'Amato | 514/323 |
| 5,736,154 | A | 4/1998 | Fuisz | 424/449 |
| 5,741,511 | A | 4/1998 | Lee et al. | 424/449 |
| 5,869,305 | A | 2/1999 | Samulski et al. | 435/172.3 |
| 5,886,039 | A | 3/1999 | Kock et al. | 514/557 |
| 5,888,767 | A | 3/1999 | Dropulić et al. | 435/69.1 |
| 5,941,868 | A | 8/1999 | Kaplan et al. | 604/500 |
| 5,962,274 | A | 10/1999 | Parks | 435/91.1 |
| 6,197,801 | B1 | 3/2001 | Lin | 514/365 |
| 6,258,374 | B1 | 7/2001 | Friess et al. | 424/436 |
| 2002/0044919 | A1 | 4/2002 | Yu | |

FOREIGN PATENT DOCUMENTS

| WO | WO 9920764 | * 4/1999 |
|---|---|---|
| WO | WO 00/58335 | * 10/2000 |
| WO | WO-2004/046191 | 6/2004 |

OTHER PUBLICATIONS

Geng et al., FASEB J. Mar. 7, 2001, vol. 15(4): p. A8, abstract 6.22.*
Phillip S., Cancer Pract. May-Jun. 2000, vol. 8(3): pp. 148-1451.*
Phillip, S., Cancer Practice, 2000, vol. 8(3), pp. 148-150.*
Folkman et al., 1976, Sci. Am., vol. 234, pp. 58-64.*
Shin et al., 2000, Cornea, vol. 19(2), pp. 212-217.*
Colorado et al., 2000, Cancer Res., vol. 60, pp. 2520-2526).*
Wassberg, Ups. J. Med. Sci., 1999, vol. 104(1):1-24, (Abstract).*
Di Bisceglie et al., Hepatology, 1998, vol. 28(4):1161-1165.*
Buckley et al., ORL J. Otorhinolaryngol.Relat. Spec., Jul.-Aug. 2001, vol. 63(4):259-264.*
Auerbach and Auerbach, Pharmacol. Ther. 63(3):265-311 (1994).
Bagri et al., Neuron 33(2):233-48 (2002).
Biochemistry 11:1726 (1972).
Brantley et al., Oncogene 21:7011-26 (2002).
Brose et al., Cell (1999) 96(6):795-806.
Liu et al., Biochem. Biophys. Res. Commun. (2001) 286:281-291.
Ma et al., J. Biol. Chem. (1994) 269:27739-27746.
Yuan et al., Dev. Biol. (1999) 212(2):290-306.
International Search Report for PCT/US03/07458, mailed on Mar. 9, 2006, 5 pages.
Wang et al., Cancer Cell (2003) 4(1):19-29.
Werner et al., J. Cancer Res. Clin. Oncol. (2001) 127:207-216.
Gordon et al., J. of Clin. Oncology (2001) 19(3):843-850.
Supplementary Partial European Search Report for EP 03716469.6, date mailed on Apr. 5, 2007, 5 pages.
EPO Communication (Office Action) dated Dec. 6, 2010, issued by the European Patent Office in related European Patent Application No. EP-03716469.6 (3 pages).

* cited by examiner

*Primary Examiner* — Elizabeth C. Kemmerer
*Assistant Examiner* — Xiaozhen Xie
(74) *Attorney, Agent, or Firm* — Osha • Liang LLP

(57) ABSTRACT

This invention is generally in the field of methods for diagnosis, treatment and prevention of various disorders involving the Slit2 mediated angiogenesis.

10 Claims, 10 Drawing Sheets

Figure 1:
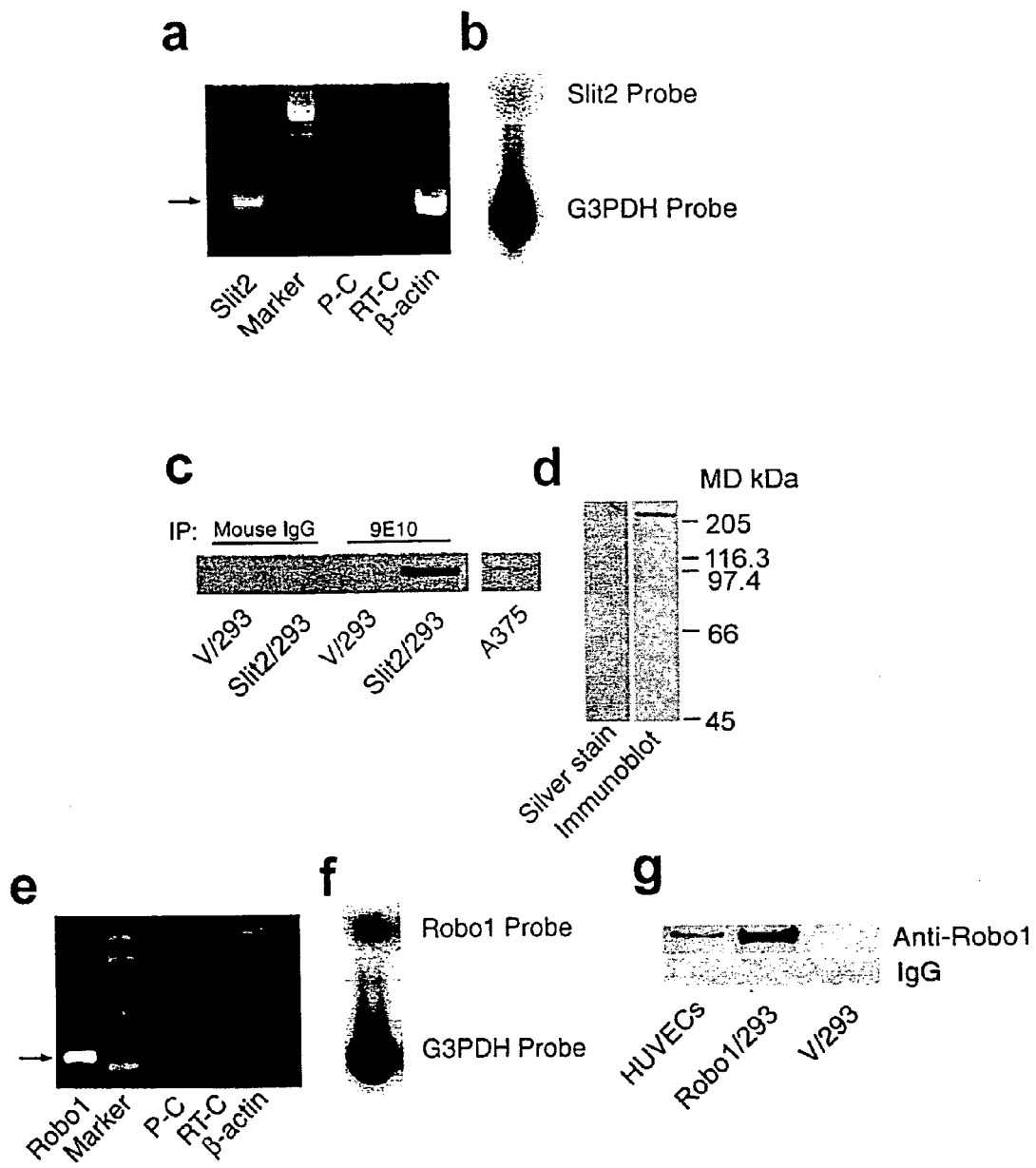
Figure 1:
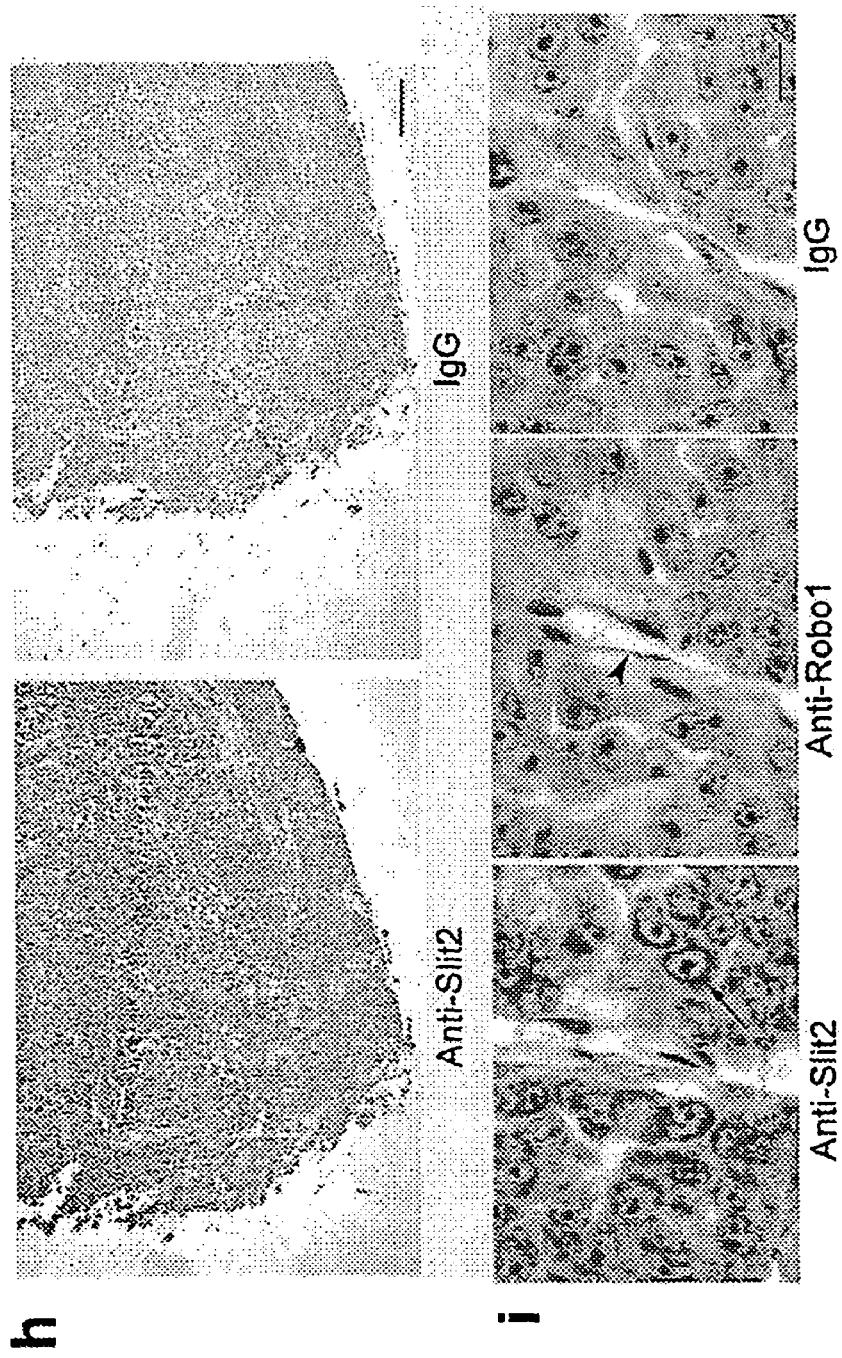

DETECTION AND MODULATION OF SLIT AND ROUNDABOUNT (ROBO) MEDIATED ANGIOGENESIS AND USES THEREOF

CROSS-REFERENCE TO RELATED APPLICATIONS

The present application claims priority benefit of U.S. Provisional Application Ser. No. 60/362,485, filed Mar. 8, 2002 under 35 U.S.C. §119(e). The content of the above-referenced application is incorporated by reference herein in its entirety.

BACKGROUND OF THE INVENTION

Angiogenesis is a cellular process of capillary sprouting and configuring of neovasculatures from the existing blood vessels. It is in contrast to another process of blood vessel formation, called vasculogenesis, whereby the blood vessels are de novo formed by the coalescence of endothelial progenitor cells. During primate development, such as embryogenesis and tissue/organ morphogenesis, blood vessels are produced by both vasculogenesis and angiogenesis. However, new vessels are formed only through angiogenesis in the adult. Except during the female reproductive cycles (ovulation, menstruation, implantation and pregnancy), the endothelial cells are quiescent and thus long-lived in the normal adult mammals. Yet, they undergo an activation process, upon appropriate stimuli, to grow into new capillaries during episodic growth and remodeling of the blood vessel network.

Angiogenesis is of crucial importance in a variety of physiological and pathological conditions and diseases, including ischemia and hypoxia, atherosclerosis, leukocyte trafficking and recruitment, hemostasis, wound healing, vascular leaky syndrome, diabetic retinopathy, macular degeneration, neovascular glaucoma, psoriasis, rheumatoid arthritis, hemangioma, and cancer growth and metastasis (Hanahan, D. and Folkman, J. *Cell* 86:353-364 (1996); Carmeliet, P. and Jain, R. K. *Nature* 407:249-257 (2000)). The importance of angiogenesis for the growth of a variety of cancers is now well recognized. For instance, the growth of solid tumors requires concomitant expanding of the vascular networks for their blood supplies; an insufficient supply of blood (more than 100 to 200 µm away from blood vessels) is known to lead to the necrosis of cancer tissues. Although vascular endothelial cell growth factor (VEGF), fibroblast growth factor (FGF), angiopoitins and other molecules are indispensable for vessel formations (Hanahan, D. *Science* 277:48-50 (1997); Yancopoulos, G. D. et al. *Nature* 407:242-248 (2000)), the molecular and cellular mechanisms governing tumor angiogenesis are still poorly understood.

In vertebrates, the vascular system is mainly for material transportation while the nervous system is mainly for information communication; notably, both of them have the circuit properties anatomically and physiologically (Shima, D. T. and Mailhos, C. *Curr. Opin. Genet. Dev.* 10:536-542 (2000)). For example, (1) capillary vessels are formed by the endothelial cells ensheathed with pericytes while nerves are composed by neurons surrounded with glia; (2) both blood vessels and nerves ramify throughout almost all the parts of the body; and (3) the circulatory system is divided by arteries (sending the blood out of the heart) and veins (send the blood back to the heart) while the nervous system has both motor nerves (sending the impulse out of the brain or the spinal cord) and sensory nerves (send the impulse back to the brain or the spinal cord). In addition to sharing of these morphological and functional features, blood vessels and nerves have an intimately physical relationship, such as the autonomic nerves that regulates the vascular tones.

It is currently known that the pathfinding of the nervous networks requires several families of neurological migratory cues, such as semaphorin, ephrin, netrin, Slit and several others. Prominent among these molecules that simultaneously promote angiogenesis is neuropilin-1, a membrane receptor of the semaphorin family expressed on both developing neurons and endothelial cells. It binds to VEGF165, a splicing isoform of the VEGF gene (Soker, S. et al. *Cell* 92:735-45 (1998)), and functionally, its mutant mouse embryos manifest severe defects of vascular formations (Kawasaki, T. et al. *Development* 126:4895-902 (1999)). Tumor cells can also express neuropilin-1, resulting in substantially enhanced tumor angiogenesis and enlarged tumors. In analog, the cell-bound ephrin ligands and their cognate Eph receptor tyrosine kinases play essential roles in vascular development. Among them, Ephrin-B2, a transmembrane ligand specifically expressed on arterial endothelial cells and surrounding cells, interacts with multiple EphB class receptors. Conversely, EphB4, a specific receptor for ephrin-B2, is expressed on venous endothelial cells. The bidirectional signals between EphB4 and ephrin-B2 are thought to be specific for the development of the arteries and veins (Wang, H. U. et al. *Cell* 93:741-53 (1998)). Further, the EphA2 receptor is up-regulated in transformed cells and tumor vasculatures where they likely contribute to cancer pathogenesis (Brantley, D. M. et al. *Oncogene* 21:7011-26 (2002)). Likewise, the rat netrin1 receptor Unc5h2 mRNA is observed during the early blood vessel formation, implicating the potential involvement of netrin and its receptors in vasculogenesis (Engelkamp, D. *Mech. Dev.* 118:191-197 (2002)).

Slit2, a member of another family of "neurological" migratory cues, is expressed by midline cells and endothelial cells. It reacts with a cell surface transmembrane protein, Roundabout1 (Robo1), and functions as a repellent in axon guidance (Kidd, T. et al. *Cell* 92:201-215 (1998); Brose, K. et al. *Cell* 96:795-806 (1999); Li, H. S. et al. *Cell* 96:807-818 (1999)) and branching (Wang, K.-H. et al. *Cell* 96:771-784 (1999); Whitford, K. L. et al. *Neuron* 33:47-61 (2002)), neuronal migration (Wu, W. et al. *Nature* 400:331-336 (1999)), and as an endogenous inhibitor for leukocyte chemotaxis (Wu, J. Y. et al. *Nature* 410:948-952 (2001)). Currently, there are three slit genes, slit1, 2 and 3 and four robo genes, robo1, robo2, rig-1 and robo4, known in the mammals. Their expressions outside the nervous system have been found in the rodents (Holmes, G. P. et al. *Mech. Dev.* 79:57-72 (1998); Piper, M. et al. *Mech. Dev.* 94: 213-217 (2000)). For example, mRNAs for Slit2 and Slit3, but not for Slit1, are found in rat endothelial cells and Robo1 RNA is found in mouse leukocytes (Wu, J. Y. et al. *Nature* 410:948-952 (2001)). Further, human endothelial cells express Robo4 (Huminiecki, L. et al. Genomics. 79:547-552 (2002)). However, it is not determined whether human cancer cells can express these genes, especially at the protein levels.

BRIEF SUMMARY OF THE INVENTION

The present invention is directed to methods, compositions and kits for preventing, treating or diagnosing a disease or disorder associated with Slit2 mediated angiogenesis.

In one aspect, the present invention is directed to a method for preventing or treating a disease or disorder associated with Slit2 mediated angiogenesis in a subject, which method comprises reducing or enhancing Slit2-Slit2 receptor interaction in a subject to a level sufficient to prevent or treat a disease or disorder associated with Slit2 mediated angiogenesis in said subject.

In another aspect, the present invention is directed to a pharmaceutical composition for preventing or treating a disease or disorder associated with Slit2 mediated angiogenesis in a subject, which pharmaceutical composition comprises an effective amount of a substance that reduces or enhances Slit2-Slit2 receptor interaction.

In still another aspect, the present invention is directed to a combination for preventing or treating a disease or disorder associated with Slit2 mediated angiogenesis in a subject, which combination comprises: a) an effective amount of a substance that reduces or enhances Slit2-Slit2 receptor interaction; and b) an effective amount of a substance that reduces or enhances angiogenesis.

In yet another aspect, the present invention is directed to a method for prognosing or diagnosing a disease or disorder associated with Slit2 mediated angiogenesis in a subject, which method comprises: a) obtaining a test sample from a test subject and assessing Slit2 and/or Slit2 receptor level in said test sample; b) obtaining a control sample from a control subject not having a disease or disorder associated with Slit2 mediated angiogenesis and assessing Slit2 and/or Slit2 receptor level in said control sample; and c) comparing Slit2 and/or Slit2 receptor levels assessed in a) and b), whereby an elevated Slit2 and/or Slit2 receptor level in said test subject relative to Slit2 and/or Slit2 receptor level in said control subject indicates that said test subject has said disease or disorder associated with Slit2 mediated angiogenesis.

In yet another aspect, the present invention is directed to a kit for prognosing or diagnosing a disease or disorder associated with Slit2 mediated angiogenesis in a subject, which kit comprises: a) a means for obtaining a test sample from a test subject and a control sample from a control subject; b) a means for assessing Slit2 and/or Slit2 receptor level in said test and control samples; and c) a means for comparing Slit2 and/or Slit2 receptor levels assessed in said test and control samples.

BRIEF DESCRIPTION OF THE SEVERAL VIEWS OF THE DRAWING(S)

FIG. 1 shows the expressions of Slit2 in A375 cells and Robo1 in Endothelial Cells. a and e, Slit2 mRNA in A375 cells and Robo1 mRNA in HUVECs were determined by semi-quantitative RT-PCR analysis. Arrows indicated the positive Slit2 and Robo1 bands. Human β-actin mRNA was assayed as controls for RT-PCR. P-C (PCR control) was PCR in the absence of the templates; RT-C (RT control) was PCR using the template generated without the reverse transcriptase. b and f, Northern blotting of Slit2 (~5.0 kb) in A375 cells and Robo1 (~4.6 kb) in HUVECs. G3PDH (a housekeeping gene) was used as the control. c and g, The protein expressions of Slit2 in A375 cells (~210 kDa) and Robo1 (~210 kDa) in HUVECs were detected by anti-Slit2 and Robo1 Abs, but not by preimmune IgG. Slit2/293 cells and Robo1/293 cells were used as the positive control while V/293 cells were used as the negative control. d, The affinity purified Slit2 was silver stained or immunoblotted with an anti-myc mAb, 9E10. h and i, The immunohistochemical staining of tumor solids with the anti-Slit2 Ab (an arrow indicated the expression of Slit2 on A375 cells), the anti-Robo1 Ab (an arrowhead indicated the expression of Robo1 on endothelial cells within the tumor) and preimmune IgG. Scale bar, 100 μm for h and 20 μm for i. Results were representative of two to ten separate experiments.

Figure 2:
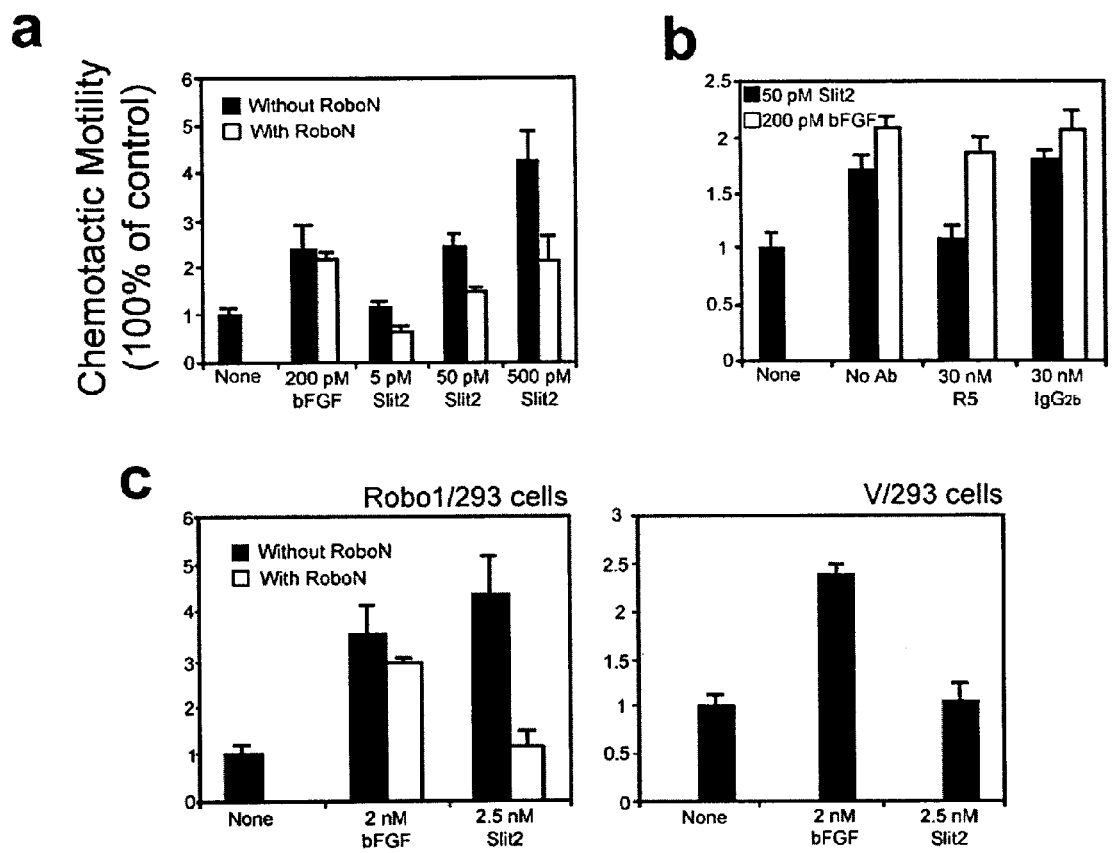
Figure 2:
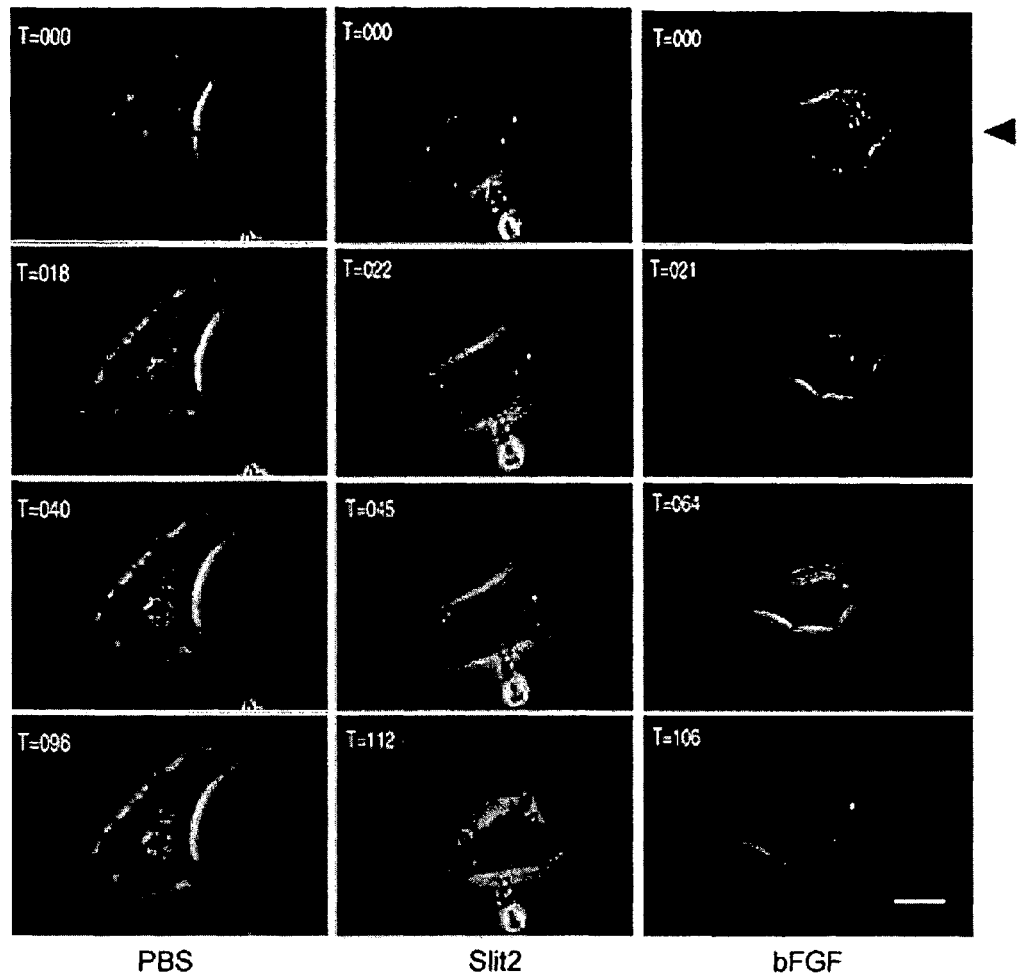
Figure 2:
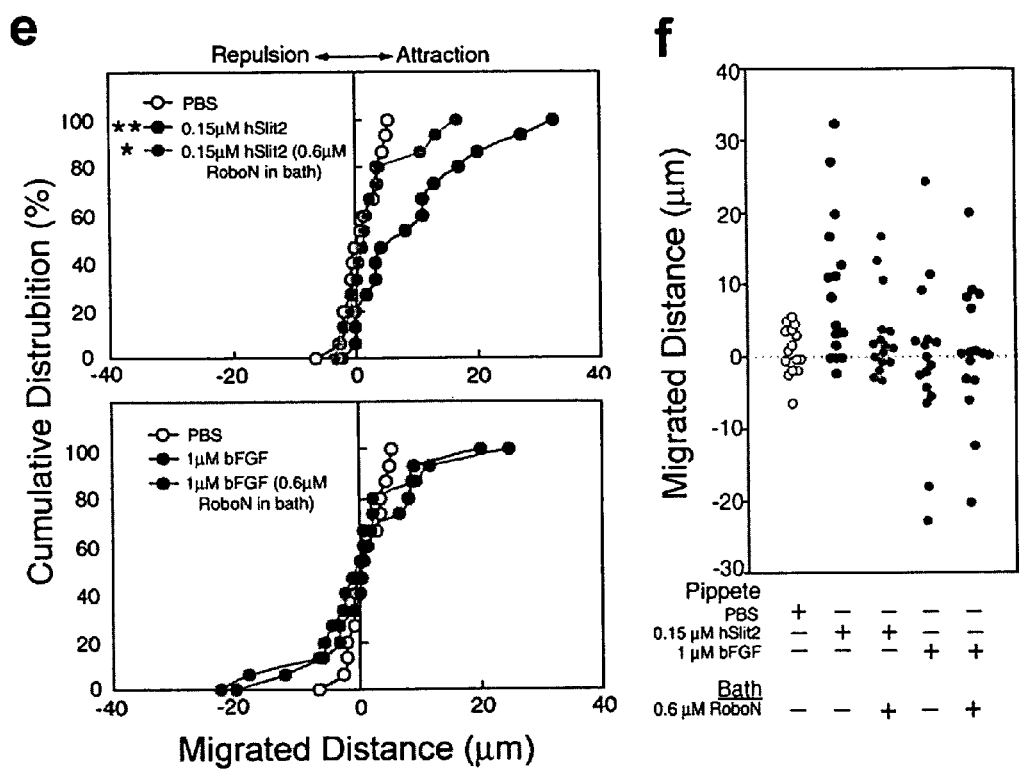
Figure 2:
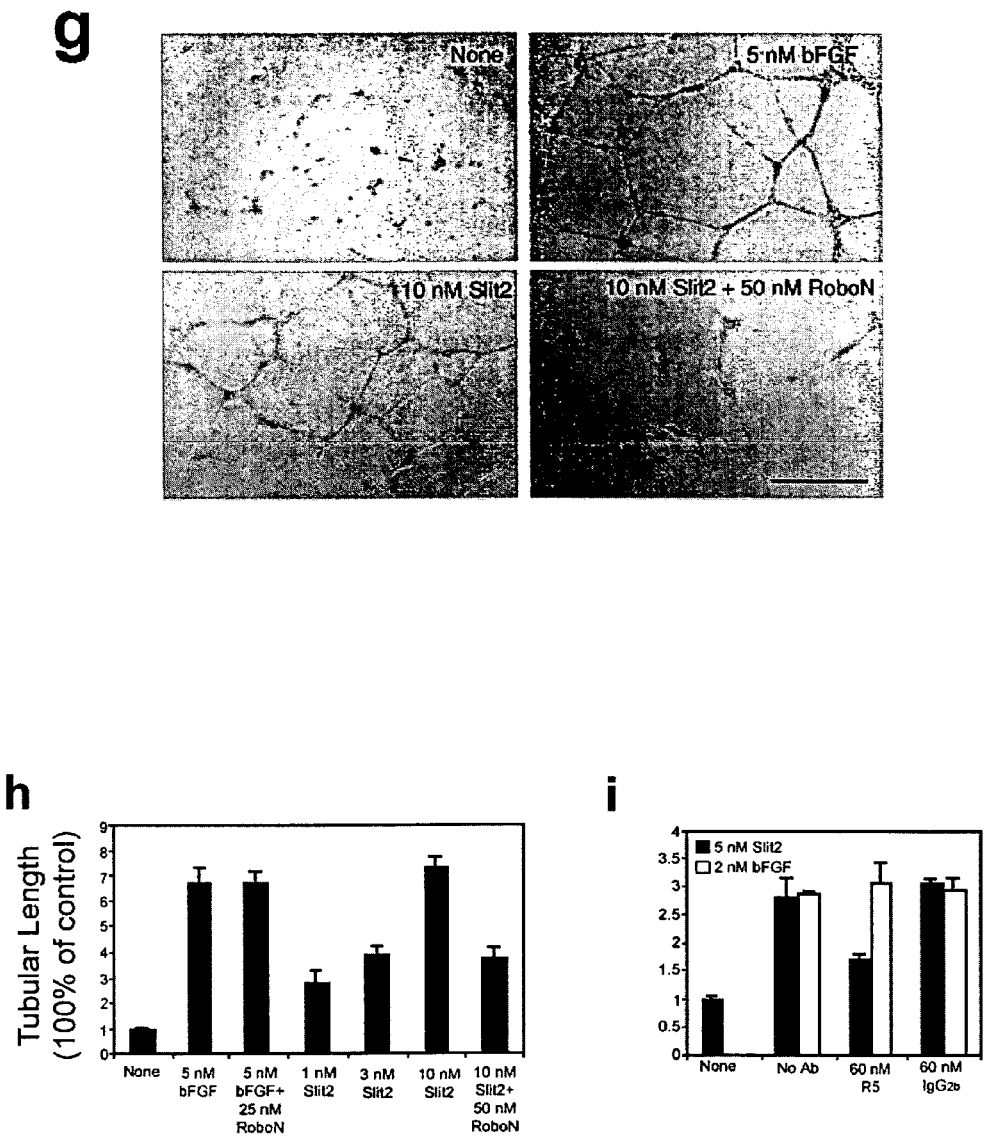

FIG. 2 shows the Slit2-induced migrations and tube formations. Migrations of HUVECs (a and b), Robo1/293 cells and 293 cells (c) were measured using Boyden chamber assay. Results were calculated as mean±S.D. values from triplicate measurements of three to six separate experiments. For the measurements of directional migrations of HUVECs, a protein gradient was applied from a micropipette by the pulsatile application of 0.15 μM Slit2 or 1 μM bFGF. Phase contrast micrographs of individual endothelial cells were recorded at indicated time points after exposure to the gradient of Slit2 or bFGF. The arrowhead indicated the directions in which the proteins were loaded through pipettes. Scale bar, 8 μm. The migratory directions induced by Slit2 and bFGF (e) and migrated distances (f) were presented (each dot representing the migratory direction and distance of single endothelial cell). g, Tube formations of HUVECs on Matrigel were visualized by phase-contrast microscopy. Scale bar, 60 μm. h and i, The effects of Slit2 and bFGF on the tube formations of HUVECs without or with RoboN or R5. Results were calculated as mean±S.D. values from triplicate of three to twenty separate experiments. *, $p<0.05$ and **, $p<0.01$ when compared with the PBS control.

Figure 3:
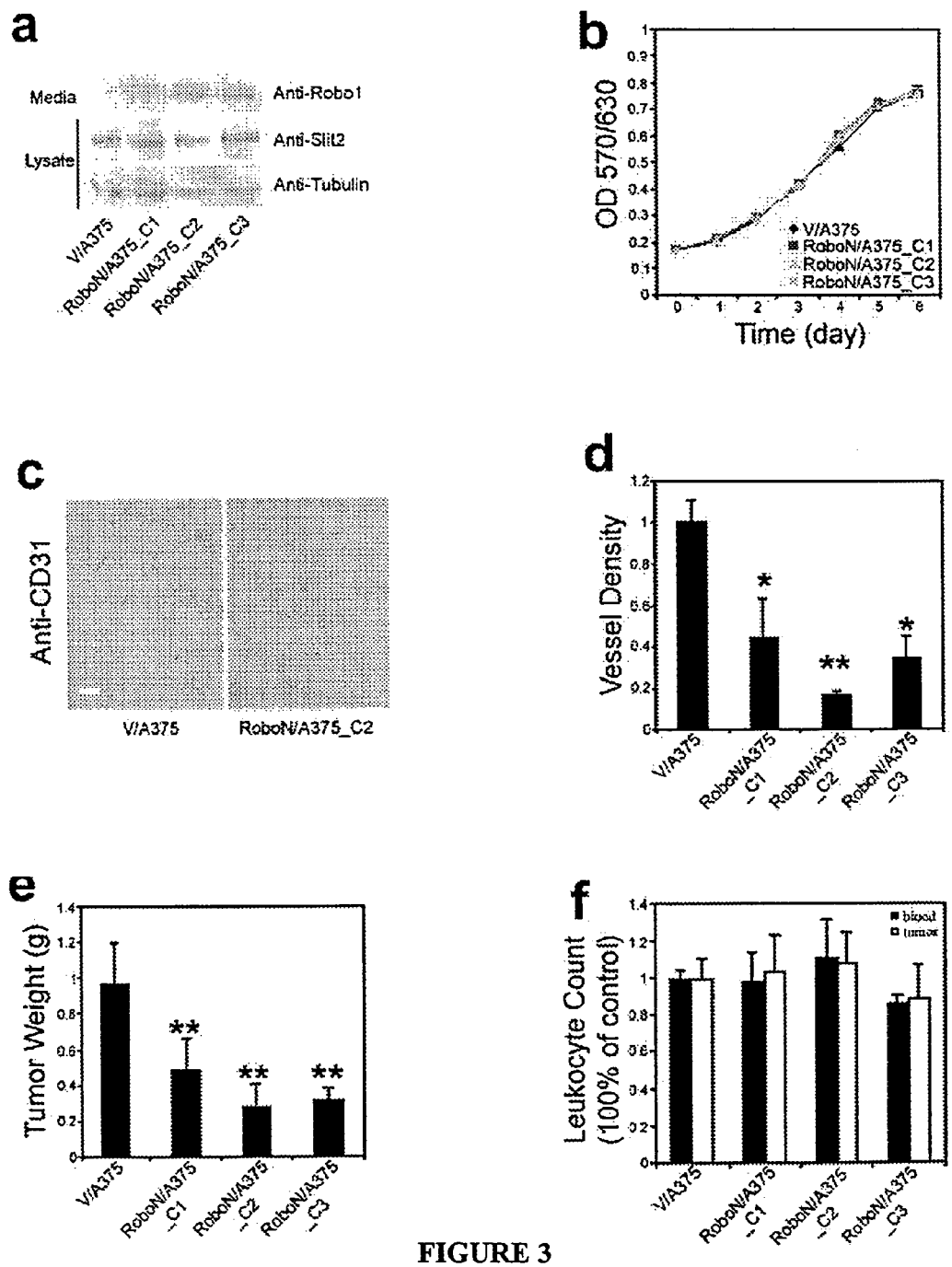
Figure 3:
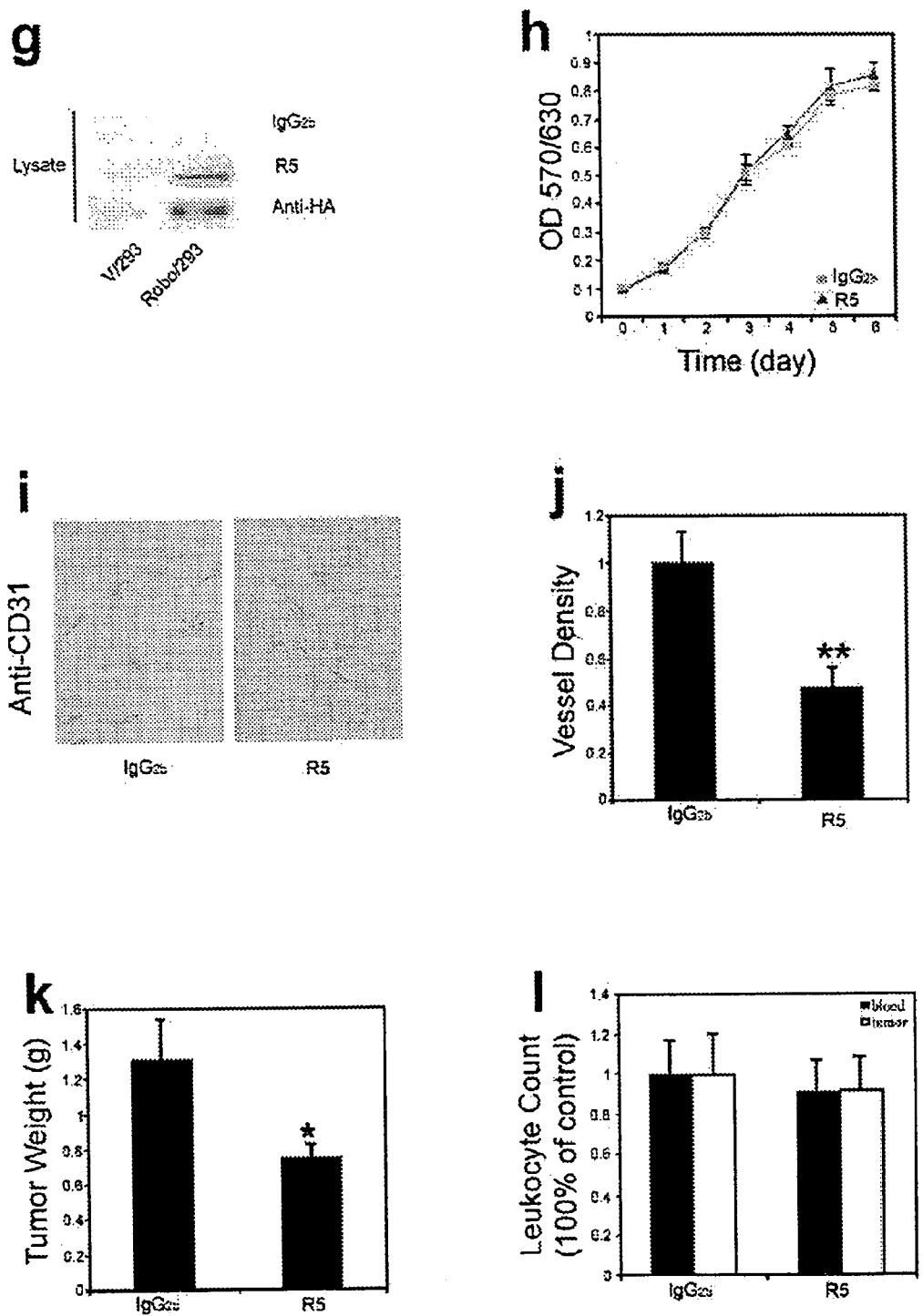

FIG. 3 shows the inhibition of tumor angiogenesis and growths of malignant melanoma. a, The detections of RoboN, Slit2 and tubulin in A375 cells following transfection with RoboN inserted vector (RoboN/A375), but not the plain vector (V/A375), by their specific Abs. No positive signals for preimmune rabbit IgG (data not shown). g, The binding of the R5 mAb to Robo1/293 cells, but not V/293 cells. The anti-hemoagglutinin polyclonal Ab (Invitrogen) was used as the positive control. b and h, The measurements of growth rates for V/A375 and RoboN/A375_C1, C2 and C3 cells (b) and for A375 cells in the presence of R5 or mouse $IgG_{2b}$ (h). Results were the mean±S.D. values from triplicate measurements of three separate experiments. c and i, The immunohistochemical staining of blood vessels within the tumor solids from V/A375 cells and RoboN/A375_C2 cells (c) and from A375 cells treated with mouse $IgG_{2b}$ and R5 (i) using an anti-CD31 Ab (PharMingen). No positive staining was detected when preimmune IgG was used (data not shown). Bar scale, 20 μm. d and j, Statistical analysis of CD31 staining was performed using the ImageTool software. The mean±S.D. values of vessel densities for tumor solids from V/A375 cells, RoboN/A375_C1, C2 and C3 cells (d) and from A375 cells treated with mouse $IgG_{2b}$ or R5 (j; n=14 for each group). e and k, The mean±S.D. values of tumor weights for tumor solids from V/A375 cells, RoboN/A375_C1, C2 and C3 cells (e) and from A375 cells treated with mouse $IgG_{2b}$ or R5 (k; n=14 for each group). f and l, The leukocyte counts in bloods and in tumors for V/A375 cells, RoboN/A375_C1, C2 and C3 cells (f) and for A375 cells treated with mouse $IgG_{2b}$ or R5 (l; n=14 for each group). *, $p<0.05$ and **, $p<0.01$.

Figure 4:
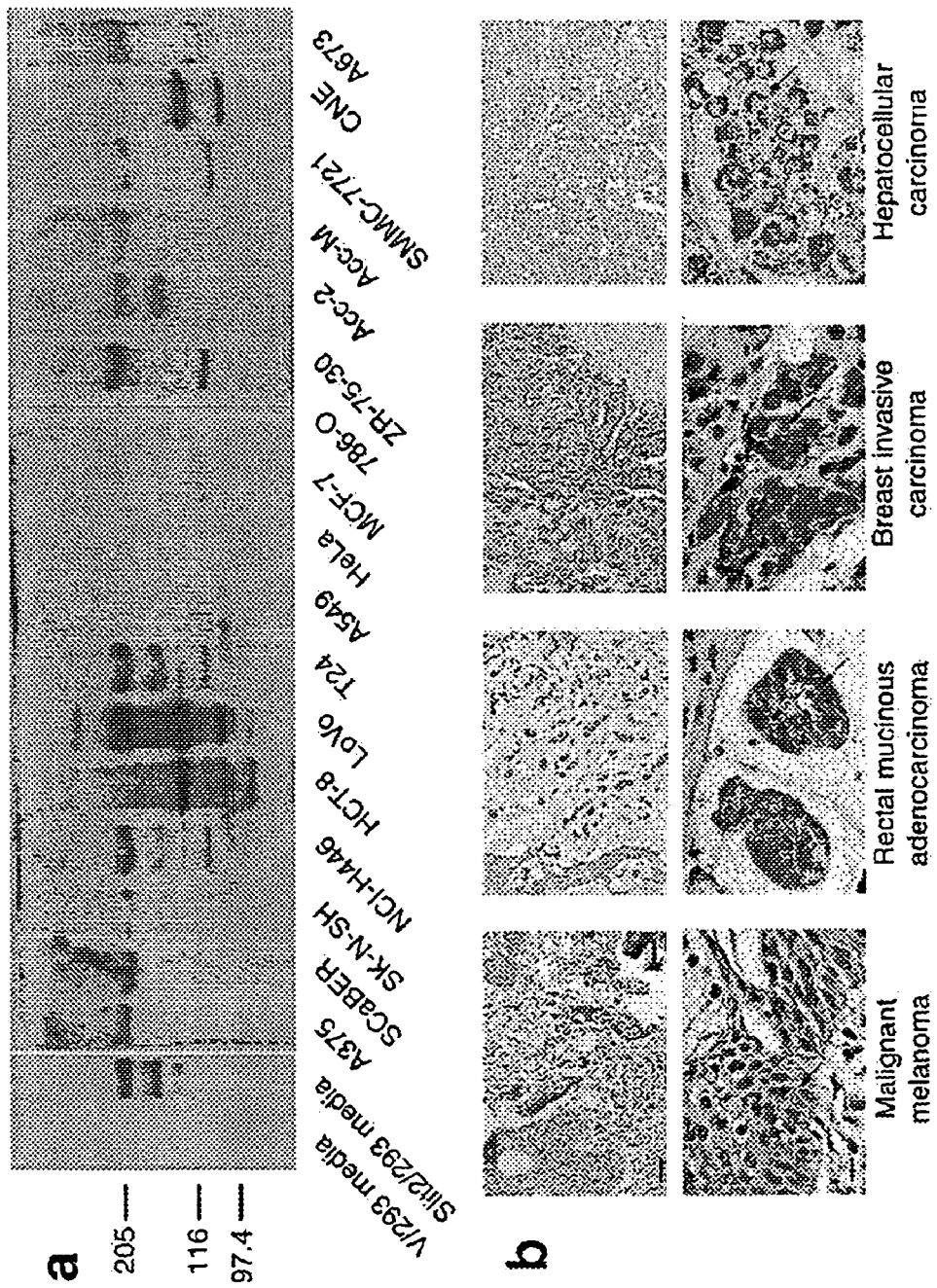
Figure 4:
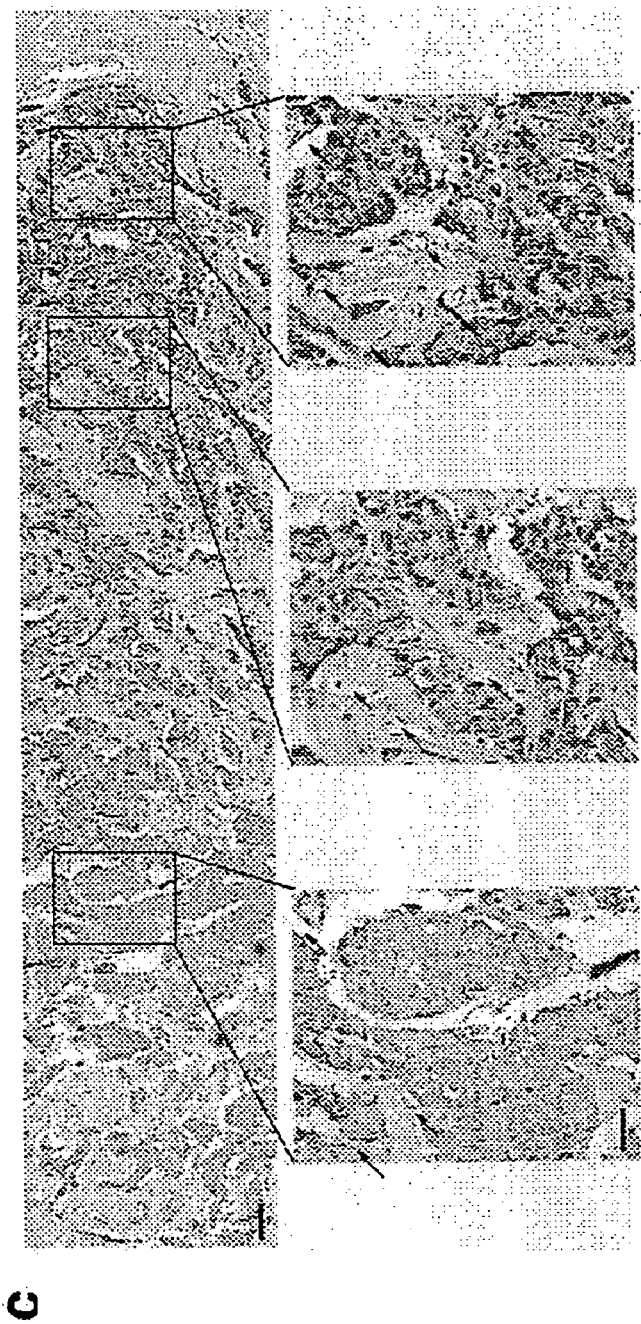

FIG. 4 shows the expressions of Slit2 in cancers. a, Immunoblotting of cell lysates from various cancer cell lines with the anti-Slit2 Ab. The Slit2/293 cells were used as the positive control while the V/293 cells were used as the negative control. b, The immunohistochemical staining of human cancers with the anti-Slit2 Ab. Arrows indicated the expression of Slit2 on tumor cells. Bar scale, 100 μm for the upper panel and 10 μm for the lower panel, respectively. c, The Slit2 gradients on human breast invasive carcinoma visualized by the staining with the anti-Slit2 Ab. Arrows indicated the microvessels within tumors. Bar scales, 100 μm for the upper panel and 40 μm for the lower panel, respectively.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "composition" refers to any mixture of two or more products or compounds. It may be a solution, a suspension, liquid, powder, a paste, aqueous, non-aqueous, or any combination thereof.

As used herein, a "combination" refers to any association between two or among more items.

As used herein, angiogenesis is intended to broadly encompass the totality of processes directly or indirectly involved in the establishment and maintenance of new vasculature (neovascularization), including, but not limited to, neovascularization associated with tumors.

As used herein, anti-angiogenic treatment or agent refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. Thus, for purposes herein an anti-angiogenic agent refers to an agent that inhibits the establishment or maintenance of vasculature. Such agents include, but are not limited to, anti-tumor agents, and agents for treatments of other disorders associated with undesirable angiogenesis, such as diabetic retinopathies, restenosis, hyperproliferative disorders and others.

As used herein, pro-angiogenic agents are agents that promote the establishment or maintenance of the vasculature. Such agents include agents for treating cardiovascular disorders, including heart attacks and strokes.

As used herein, undesired and/or uncontrolled angiogenesis refers to pathological angiogenesis wherein the influence of angiogenesis stimulators outweighs the influence of angiogenesis inhibitors.

As used herein, deficient angiogenesis refers to pathological angiogenesis associated with disorders where there is a defect in normal angiogenesis resulting in aberrant angiogenesis or an absence or substantial reduction in angiogenesis.

As used herein, "Slit2" refers to a member of the Slit family of "neurological" migratory cues. It is expressed by midline cells and endothelial cells and functions as a repellent in axon guidance (Kidd, T. et al. *Cell* 92:201-215 (1998); Brose, K. et al. *Cell* 96:795-806 (1999); Li, H. S. et al. *Cell* 96:807-818 (1999)) and branching (Wang, K.-H. et al. *Cell* 96:771-784 (1999); Whitford, K. L. et al. *Neuron* 33:47-61 (2002)), neuronal migration (Wu, W. et al. *Nature* 400:331-336 (1999)), and as an endogenous inhibitor for leukocyte chemotaxis (Wu, J. Y. et al. *Nature* 410:948-952 (2001)). Currently, there are three slit genes, slit1, 2 and 3, known in the mammals. Their expressions outside the nervous system have been found in the rodents (Holmes, G. P. et al. *Mech. Dev.* 79:57-72 (1998); Piper, M. et al. *Mech. Dev.* 94: 213-217 (2000)). For example, mRNAs for Slit2 and Slit3, but not for Slit1, are found in rat endothelial cells (Wu, J. Y. et al. *Nature* 410:948-952 (2001)).

As used herein, "Robo1" refers to a member of Robo family of "neurological" migratory cues. It is a cell surface transmembrane protein expressed by neurons. It reacts with Slit2 and functions as a repellent in axon guidance (Kidd, T. et al. *Cell* 92:201-215 (1998); Brose, K. et al. *Cell* 96:795-806 (1999); Li, H. S. et al. *Cell* 96:807-818 (1999)) and branching (Wang, K.-H. et al. *Cell* 96:771-784 (1999); Whitford, K. L. et al. *Neuron* 33:47-61 (2002)), neuronal migration (Wu, W. et al. *Nature* 400:331-336 (1999)), and as an endogenous inhibitor for leukocyte chemotaxis (Wu, J. Y. et al. *Nature* 410:948-952 (2001)). Currently, there are four robo genes, robo1, robo2, rig-1 and robo4, known in the mammals. Their expressions outside the nervous system have been found in the rodents (Holmes, G. P. et al. *Mech. Dev.* 79:57-72 (1998); Piper, M. et al. *Mech. Dev.* 94: 213-217 (2000)). For example, Robo1 RNA is found in mouse leukocytes (Wu, J. Y. et al. *Nature* 410:948-952 (2001)). Further, human endothelial cells express Robo4 (Huminiecki, L. et al. Genomics. 79:547-552 (2002)).

As used herein, the terms "pharmaceutically acceptable salts" or "pharmaceutically acceptable derivatives" of the compounds of the present invention encompass any salts, esters or derivatives that may be readily prepared by those of skill in this art. Pharmaceutically acceptable salts of the compounds of this invention include, for example, those derived from pharmaceutically acceptable inorganic and organic acids and bases. Salts derived from appropriate bases include, but are not limited to, alkali metal (e.g., sodium), alkaline earth metal (e.g., magnesium), ammonium and $N(C_{1-4}$ alkyl$)_4^+$ salts. Examples of suitable acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic, and benzenesulfonic acids. Other acids, such as oxalic, while not in themselves pharmaceutically acceptable, may be employed in the preparation of salts useful as intermediates in obtaining the compounds of the invention and their pharmaceutically acceptable acid salts.

As used herein, biological activity refers to the in vivo activities of a compound or physiological responses that result upon in vivo administration of a compound, composition, or other mixture. Biological activity, thus, encompasses therapeutic effects and pharmaceutical activity of such compounds, compositions and mixtures. Biological activities may be observed in in vitro systems designed to test or use such activities.

As used herein, "fluid" refers to any composition that can flow. Fluids thus encompass compositions that are in the form of semi-solids, pastes, solutions, aqueous mixtures, gels, lotions, creams, and other such compositions.

As used herein, the abbreviations for any protective groups, amino acids and other compounds, are in accord with their common usage, recognized abbreviations, or the IUPAC-IUB Commission on Biochemical Nomenclature, unless otherwise indicated (see *Biochemistry* 11:1726 (1972)).

As used herein, "disease or disorder" refers to a pathological condition in an organism, which is characterizable by identifiable symptoms.

As used herein, the term "a therapeutic agent" refers to any conventional drug or drug therapies which are known to those skilled in the art, including, but not limited to vaccines.

As used herein, "vaccine" refers to any compositions intended for active immunological prophylaxis. A vaccine may be used therapeutically to treat a disease, to prevent development of a disease, or to decrease the severity of a disease either proactively or after infection. Exemplary vaccines include, but are not limited to, preparations of killed microbes of virulent strains, living microbes of attenuated (variant or mutant) strains, or microbial, fungal, plant, protozoa, or metazoa derivatives or products. The term also encompasses protein/peptide and nucleotide based vaccines.

As used herein, the term "effective amount" refers to that amount that is sufficient to ameliorate, or in some manner reduce the symptoms associated with the disease. Such amount may be administered as a single dosage or according to a regimen. Repeated administration may be required to achieve the desired amelioration of symptoms.

As used herein, the terms "administration" or "administering" a compound refers to any suitable method of providing a compound of the invention or a pro-drug of a compound of the invention to a subject.

As used herein, the term "treatment" refers to any manner in which the symptoms of a condition, disorder or disease are ameliorated or otherwise beneficially altered. Treatment also encompasses any pharmaceutical use of the compositions herein. Amelioration of symptoms of a particular disorder refers to any lessening of symptoms, whether permanent or temporary, that can be attributed to or associated with administration of the composition.

As used herein, an anti-neoplastic treatment refers to any treatment designed to treat the neoplasm, tumor or cancer by lessening or ameliorating its symptoms. Treatments that prevent the occurrence or lessen the severity of neoplasm, tumor or cancer are also contemplated.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, an anti-neoplasm agent (used interchangeably with anti-neoplastic agent, anti-tumor or anti-cancer agent) refers to any agents used in the anti-neoplasm treatment. These include any agents, that when used alone or in combination with other compounds, can alleviate, reduce, ameliorate, prevent, place or maintain in a state of remission clinical symptoms or diagnostic markers associated with neoplasm, tumor or cancer. The anti-neoplasm agent that can be used in the combinations of the present invention include, but are not limited to, anti-angiogenic agents, alkylating agents, antimetabolite, certain natural products, platinum coordination complexes, anthracenediones, substituted ureas, methylhydrazine derivatives, adrenocortical suppressants, certain hormones and antagonists, anti-cancer polysaccharides, and certain herb extracts such as Chinese herb extracts.

As used herein, "tumor suppressor gene" (also referred to as anti-oncogene or cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wilm's tumor), DCC (deleted in colonic carcinoma), NF-1 (neurofibrosarcoma) and APC (adenomatous polypospis coli).

As used herein, "oncogene" refers to a mutated and/or overexpressed version of a normal gene of animal cells (the proto-oncogene) that in a dominant fashion can release the cell from normal restraints on growth. Thus, an oncogene alone, or in concert with other changes, converts a cell into a tumor cell. Exemplary oncogenes include, but are not limited to, abl, erbA, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

As used herein, "antisense polynucleotides" refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand.

As used herein, "antibody" includes antibody fragments, such as Fab fragments, which are composed of a light chain and the variable region of a heavy chain.

As used herein, "humanized antibodies" refers to antibodies that are modified to include "human" sequences of amino acids so that administration to a human will not provoke an immune response. Methods for preparing such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, an "antibody fragment" refers to any derivative of an antibody that is less then full length, retaining at least a portion of the full-length antibody's specific binding ability. Examples of antibody fragments include, but are not limited to, Fab, Fab', F (ab) 2, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, "amelioration of the symptoms of a particular disorder by administration of a particular pharmaceutical composition" refers to any lessening, whether permanent or temporary, lasting or transient that can be attributed to or associated with administration of the composition.

As used herein "assessing" is intended to include quantitative and qualitative determination in the sense of obtaining an absolute value for the Slit2 and/or Slit2 ligand level, present in the sample, and also of obtaining an index, ratio, percentage, visual or other value indicative of the level of the activity. Assessment may be direct or indirect and the chemical species actually detected need not of course be the proteolysis product itself but may for example be a derivative thereof or some further substance.

As used herein, "a therapeutic agent, therapeutic regimen, radioprotectant, chemotherapeutic" mean conventional drugs and drug therapies, including vaccines, which are known to those skilled in the art. Radiotherapeutic agents are well known in the art.

As used herein, "treatment" means any manner in which the symptoms of a conditions, disorder or disease are ameliorated or otherwise beneficially altered. Treatment also encompasses any pharmaceutical use of the compositions herein.

B. Methods for Preventing or Treating a Disease or Disorder Associated with Slit2 Mediated Angiogenesis In one aspect, the present invention is directed to a method for preventing or treating a disease or disorder associated with Slit2 mediated angiogenesis in a subject, which method comprises reducing or enhancing Slit2-Slit2 ligand interaction in a subject to a level sufficient to prevent or treat a disease or disorder associated with Slit2 mediated angiogenesis in said subject.

The present methods can be used to prevent or treat a disease or disorder associated abnormally high or low level of Slit2 mediated angiogenesis. In one example, the disease or disorder is associated with abnormally high level of Slit2 mediated angiogenesis and the Slit2-Slit2 receptor interaction is reduced to prevent or treat the disease or disorder. In anther example, the disease or disorder is associated with abnormally low level of Slit2 mediated angiogenesis and the Slit2-Slit2 receptor interaction is enhanced to prevent or treat the disease or disorder.

The Slit2-Slit2 receptor interaction can be reduced or enhanced by any suitable methods. For example, the Slit2-Slit2 receptor interaction can be reduced or enhanced via administering to the subject an effective amount of a substance that reduces or enhances replication of Slit2 gene, replication of Slit2 ligand gene, transcription of Slit2 gene, transcription of Slit2 ligand gene, splicing or translation of Slit2 mRNA, splicing or translation of Slit2 receptor mRNA, maturation or cellular trafficking of Slit2 precursor, or maturation or cellular trafficking of Slit2 ligand precursor.

In anther example, the Slit2-Slit2 receptor interaction can be reduced or prevented via administering to the subject an effective amount of a substance that reduces or enhances Slit2-Slit2 receptor protein-protein interaction. Any suitable substance can be used to reduce or prevent the Slit2-Slit2 receptor protein-protein interaction. Such exemplary substances include an anti-Slit2 antibody, an anti-Slit2 receptor antibody and a Slit2 receptor fragment derived from extracellular domain of the Slit2 receptor that is capable of binding to Slit2. Any suitable anti-Slit2 antibody or anti-Slit2 receptor antibody can be used to reduce or prevent the Slit2-Slit2 receptor protein-protein interaction, e.g., a polyclonal antibody, a monoclonal antibody, a Fab fragment and a F(ab')$_2$ fragment.

The present methods can be used to prevent or treat a disease or disorder associated with any Slit2 mediated angiogenesis, including angiogenesis mediated by Slit2 disclosed in the following references or GenBank Accession Nos.: Dallol et al., Cancer Res Oct. 15, 2002; 62(20):5874-80; Nguyen-Ba-Charvet et al., J Neurosci Jul. 1, 2002; 22(13): 5473-80; Ozdinler and Erzurumlu, J Neurosci Jun. 1, 2002; 22(11):4540-9; Plump et al., Neuron Jan. 17, 2002; 33(2): 219-32; Hu, Nat Neurosci July 2001; 4(7):695-701; Nguyen Ba-Charvet et al., J Neurosci Jun. 15, 2001; 21(12):4281-9; Niclou et al., J Neurosci Jul. 1, 2000; 20(13):4962-74; XM_132035 (*Mus musculus* slit homolog 2 (Drosophila); NM_022632 (*Rattus norvegicus* slit homolog 2 (Drosophila), Liang et al., J. Biol. Chem. 274 (25), 17885-17892 (1999)); NM_131735 (*Danio rerio* slit (Drosophila) homolog 2, Yeo et al., Dev. Biol. 230 (1), 1-17 (2001); and Hutson, L. D. and Chien, Neuron 33 (2), 205-217 (2002)); AK027326 (*Homo sapiens* cDNA FLJ14420 fis, clone HEMBA1005581, highly similar to *Homo sapiens* SLIT2); AF210321 (*Danio rerio* Slit2, Yeo et al., Dev. Biol. 230 (1), 1-17 (2001)); NM_004787 (*Homo sapiens* slit homolog 2, Itoh et al., Brain Res. Mol. Brain Res. 62 (2), 175-186 (1998); Holmes et al., Mech. Dev. 79 (1-2), 57-72 (1998); Wang et al., Cell 96 (6), 771-784 (1999); Brose et al., Cell 96 (6), 795-806 (1999)); AF144628 (*Mus musculus* SLIT2, Yuan et al., Dev. Biol. 212 (2), 290-306 (1999)); AF133270 (*Homo sapiens* SLIT2, Wang et al., Cell 96 (6), 771-784 (1999); and Brose et al., Cell 96 (6), 795-806 (1999)); and AF055585 (*Homo sapiens* neurogenic extracellular slit protein Slit2, Holmes et al., Mech. Dev. 79 (1-2), 57-72 (1998)).

The present methods can be used to prevent or treat a disease or disorder associated with any Slit2 receptor mediated angiogenesis. For example, the present methods can be used to prevent or treat a disease or disorder associated with any Slit2-Robo1 or Slit2-Robo4 mediated angiogenesis. The Slit2-Robo1 or Slit2-Robo4 interaction can be reduced or enhanced by any suitable methods. Preferably, the Slit2-Robo1 or Slit2-Robo4 interaction is reduced or prevented via administering to the subject an effective amount of a substance that reduces or prevents Slit2-Robo1 or Slit2-Robo4 protein-protein interaction. Such exemplary substance can be an anti-Slit2 antibody, an anti-Robo1 antibody, an anti-Robo4 antibody, a Robo1 fragment derived from extracellular domain of the Robo1 that is capable of binding to Slit2, and a Robo4 fragment derived from extracellular domain of the Robo4 that is capable of binding to Slit2.

Any suitable anti-Slit2 antibody can be used, e.g., the anti-Slit2 antibody disclosed in Hu, Neuron August 1999; 23(4): 703-11. Any suitable anti-Robo1 antibody can be used, e.g., the anti-Robo1 antibody disclosed in Hivert et al., Mol Cell Neurosci December 2002; 21(4):534-45. Preferably, the anti-Robo1 antibody is an antibody against the first immunoglobulin domain of Robo1. More preferably, the antibody against the first immunoglobulin domain of Robo1 is R5. Any suitable Robo1 fragment derived from extracellular domain of Robo1 can be used, e.g., RoboN.

The present methods can be used to prevent or treat a disease or disorder associated with any Robo1 mediated angiogenesis, including angiogenesis mediated by Robo1 disclosed in the following references or GenBank Accession Nos.: Hivert et al., Mol Cell Neurosci December 2002; 21(4): 534-45; Clark et al., FEBS Lett Jul. 17, 2002; 523(1-3):12-6; Dallol et al., Oncogene May 2, 2002; 21(19):3020-8; Xian et al., Proc Natl Acad Sci USA Dec. 18, 2001; 98(26):15062-6; XM_139669 (*Mus musculus* roundabout homolog 1); NM_022188 (*Rattus norvegicus* roundabout homolog 1, Kidd et al., Cell 92 (2), 205-215 (1998)); AK095256 (*Homo sapiens* cDNA FLJ37937 fis, clone CTONG2007272, highly similar to *Homo sapiens* roundabout 1); NM_133631 (*Homo sapiens* roundabout, axon guidance receptor, homolog 1, Kidd et al., Cell 92 (2), 205-215 (1998)); NM_002941 (*Homo sapiens* roundabout, axon guidance receptor, homolog 1, Kidd et al., Cell 92 (2), 205-215 (1998)); AF304130 (*Danio rerio* transmembrane receptor Roundabout1, Challa et al., Mech. Dev. 101 (1-2), 249-253 (2001)); AK025535 (*Homo sapiens* cDNA: FLJ21882 fis, clone HEP02791, highly similar to AF040990 *Homo sapiens* roundabout 1, AF041082 (*Rattus norvegicus* transmembrane receptor Robo1, Kidd et al., Cell 92 (2), 205215 (1998)); AF040990 (*Homo sapiens* roundabout 1, Kidd et al., Cell 92 (2), 205-215 (1998)).

The present methods can be used to prevent or treat a disease or disorder associated with any Robo4 mediated angiogenesis, including angiogenesis mediated by Robo4 disclosed in the following references or GenBank Accession Nos.: NM_019055 (*Homo sapiens* roundabout homolog 4); NM_028783 (*Mus musculus* roundabout homolog 4, Huminiecki et al., Genomics 79 (4), 547-552 (2002); and Nature 420, 563-573 (2002)); and AF361473 (Huminiecki et al., Genomics April 2002; 79(4):547-52).

The substance can be administered by itself. Preferably, the substance is administered with a pharmaceutically acceptable carrier or excipient.

The present methods can be used to prevent or treat any disease or disorder associated with Slit2 mediated angiogenesis, e.g., ischemia and hypoxia, atherosclerosis, leukocyte trafficking and recruitment, hemostasis, wound healing, vascular leaky syndrome, diabetic retinopathy, macular degeneration, neovascular glaucoma, psoriasis, rheumatoid arthritis, hemangioma and cancer. Preferably, the cancer is metastatic. Also preferably, cancer is malignant melanoma, bladder squamous carcinoma, neuroblastoma, small cell lung cancer, colon adenocarcinoma, bladder transitional cell carcinoma, breast cancer, adenoid cystic carcinoma of salivary gland, hepatocellular carcinoma or rhabdomyosarcoma.

The present methods can be used to prevent or treat any disease or disorder associated with Slit2 mediated angiogenesis in any subject. Preferably, the subject is a mammal. More preferably, the mammal is a human.

In a specific embodiment, the subject is a human and the substance to be administered to the human is a humanized monoclonal antibody.

C. Pharmaceutical Compositions and Combinations for Preventing or Treating a Disease or Disorder Associated with Slit2 Mediated Angiogenesis In another aspect, the present invention is directed to a pharmaceutical composition for preventing or treating a disease or disorder associated with Slit2 mediated angiogenesis in a subject, which pharmaceutical composition comprises an effective amount of a substance that reduces or enhances Slit2-Slit2 receptor interaction. Preferably, the Slit2 receptor is Robo1 or Robo4. Also preferably, the pharmaceutical composition further comprises a pharmaceutically acceptable carrier or excipient.

Pharmaceutical compositions of the present invention comprise any of the substance that reduces or enhances Slit2-Slit2 receptor interaction and pharmaceutically acceptable salts thereof, alone or in combination with any pharmaceutically acceptable carriers, adjuvant or vehicle. Acceptable compositions and methods for their administration that can be employed for use in this invention include, but are not limited to those described in U.S. Pat. Nos. 5,736,154; 6,197,801; 5,741,511; 5,886,039; 5,941,868; 6,258,374 and 5,686,102. Examples of pharmaceutically acceptable carriers, adjuvants and vehicles that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The formulation, dosage and route of administration can be determined according to methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Biopharmaceutical Drug Design and Development*, Wu-Pong and Rojanasakul (Ed.), Humana Press, 1999). In the treatment or prevention of a disease or disorder associated with Slit2 mediated angiogenesis, an appropriate dosage level will generally be about 0.01 to 500 mg per kg body weight per day. Preferably, the dosage level will be about 0.1 to about 250 mg/kg per day. In more preferred embodiments, the dosage level will range from about 0.1 to about 20 mg/kg per day. The appropriate dosage can be administered in single or multiple dose. It will be understood that the specific dose level and frequency of dosage for any particular subject may be varied and will depend upon a variety of factors, including the activity of the specific compound used, the metabolic stability and length of action of that compound, the age, body weight, general health, sex, diet, mode and time of administration, rate of excretion, drug combination, the severity of the particular condition, and the patient undergoing therapy.

The pharmaceutical compositions of this invention can be administered orally, parenterally, by inhalation spray, topically, rectally, nasally, buccally, vaginally, via an implanted reservoir, or any suitable form of administration. The term parenteral as used herein includes subcutaneous, intracutaneous, intravenous, intramuscular, intra-articular, intrasynovial, intrasternal, intrathecal, intralesional and intracranial injection or infusion techniques. The most suitable route in any given case will depend on the nature and severity of the condition being treated and on the nature of the substance that reduces or enhances Slit2-Slit2 receptor interaction being used.

The pharmaceutical compositions may be in the form of a sterile injectable preparation, for example, as a sterile injectable aqueous or oleaginous suspension. This suspension may be formulated according to techniques known in the art using suitable dispersing or wetting agents (e.g., Tween 80), and suspending agents. The sterile injectable preparation may also be a sterile injectable solution or suspension in a non-toxic parenterally-acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, commonly used carriers include, but are not limited to, lactose and corn starch. Lubricating agents, such as magnesium stearate, can also be added. For oral administration in a capsule form, useful diluents include lactose and dried corn starch. When aqueous suspensions are administered orally, the active ingredient is combined with emulsifying and suspending agents. If desired, certain sweetening, flavoring, and coloring agents may be added.

The pharmaceutical compositions of this invention may also be administered in the form of suppositories for rectal administration. These compositions can be prepared by mixing a compound of this invention with a suitable non-irritating excipient. In particular embodiments, the excipient is solid at room temperature but liquid at the rectal temperature. Thus, the excipient will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation. For example, such composition may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of this invention may also be administered topically. For topical application to the skin, the pharmaceutical composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The invention also provides kits for carrying out the therapeutic regimens of the invention. Such kits comprise therapeutically effective amounts of a substance that reduces or enhances Slit2-Slit2 ligand interaction, alone or in combination with other agents, in pharmaceutically acceptable form. Preferred pharmaceutical forms include inhibitors in combination with sterile saline, dextrose solution, buffered solution, or other pharmaceutically acceptable sterile fluid. Alternatively, the composition may be lyophilized or desiccated. In this instance, the kit may further comprise a pharmaceutically acceptable solution, preferably sterile, to form a solution for injection purposes. In another embodiment, the kit may further comprise a needle or syringe, preferably packaged in sterile form, for injecting the composition. In other embodiments, the kit further comprises an instruction means for administering the composition to a subject. The instruction means can be a written insert, an audiotape, an audiovisual tape, or any other means of instructing the administration of the composition to a subject.

In still another aspect, the present invention is directed to a combination for preventing or treating a disease or disorder associated with Slit2 mediated angiogenesis in a subject, which combination comprises: a) an effective amount of a substance that reduces or enhances Slit2-Slit2 ligand interaction; and b) an effective amount of a substance that reduces or enhances angiogenesis.

Any anti-angiogenic agents, including those described herein, when used alone or in combination with other compounds, that can alleviate, reduce, ameliorate, prevent, or place or maintain in a state of remission of clinical symptoms or diagnostic markers associated with undesired and/or uncontrolled angiogenesis, particularly solid neoplasms, vascular malformations and cardiovascular disorders, chronic inflammatory diseases and aberrant wound repairs, circulatory disorders, crest syndromes, dermatological disorders, or ocular disorders, can be used in the combinations.

In a specific embodiment, the anti-angiogenic agent used in the combination is an inhibitor of basement membrane degradation, an inhibitor of cell migration, an inhibitor of endothelial cell proliferation, an inhibitor of three-dimensional organization and establishment of patency, or a physiological or physical anti-angiogenic treatment.

Examples of anti-angiogenic agents include, but are not limited to, protease inhibitors, endostatin, taxol, TGF-, FGF inhibitors (see, Auerbach and Auerbach, Pharmacol. Ther., 63 (3): 265-311 (1994) for a comprehensive listing of well known anti-angiogenic agents). Particular anti-angiogenic agents used in the combination include AGM-1470 (TNP-470), angiostatic steroids, angiostatin, antibodies against av 3, antibodies against bFGF, antibodies against IL-1, antibodies against TNF-a, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, marimastat (BB-2516), medroxyprogesterone, Metastat (Col-3), methotrexate, minocycline, nitric oxide, octreotide (somatostatin analogue), Paclitaxel, D-penicillamine, pentosan polysulfate, placental proliferin-related protein, placenta Rnase inhibitor, plasminogen activator inhibitor (PAls), platelet factor-4 (PF4), prednisolone, prolactin (16-Kda fragment), proliferin-related protein, prostaglandin synthase inhibitor, protamine, retinoids, Roquinimex (LS-2616. linomide), somatostatin, substance P, suramin, SU 101, tecogalan sodium (DS-4152), tetrahydrocortisol-sthrombospondins (TSPs), tissue inhibitor of metalloproteinases (TIMP 1, 2, 3), vascular endothelial growth factor inhibitors, vitamin A, Vitaxin, vitreous fluids, thalidomide, 3-aminothalidomide, 3-hydroxythalidomide and metabolites or hydrolysis products of thalidomide, 3-aminothalidomide, or 3-hydroxythalidomide ((O'Reilly, Investigational New Drugs, 15:5-13 (1997); J. Nat'l Cancer Instit., 88:786-788 (1996); U.S. Pat. Nos. 5,593,990, 5,629,327 and 5,712,291). c. Pro-angiogenic agent Any pro-angiogenic agents, including those described herein, when used alone or in combination with other compounds, that can promote physiological angiogenesis, particularly angiogenesis involved in normal placental, embryonic, fetal and post-natal development and growth, physiologically cyclical development in the ovarian follicle, corpus luteum and post-menstrual endometrium or wound healing, can be used in the present combinations.

The pro-angiogenic agent used in the combination can be a proangiogenic cytokine (Desai and Libutti, J. Immunother., 22 (3): 186-211 (1999)). More preferably, the pro-angiogenic cytokine used is a basic fibroblast growth factor such as bFGF and FGF-2, a vascular endothelial growth factor/vascular permeability factor such as VEGF/VPF and vasculotropin, a platelet-derived endothelial cell growth factor such as PD-EDGF and thymidine phosphorylase, a transforming growth factor-beta (TGF-), or angiopoietin-1 (Ang-1).

For treating cancer, any anti-neoplasm agent can be used in the combination of the present invention. Examples of anti-neoplasm agents that can be used in the compositions and methods of the present invention are described in U.S. Patent Application No. 2002/044919. In one embodiment, the anti-neoplasm agent used is an anti-angiogenic agent. The anti-angiogenic agent can be an inhibitor of basement membrane degradation, an inhibitor of cell migration, an inhibitor of endothelial cell proliferation, and an inhibitor of three-dimensional organization and establishment of potency. Examples of such anti-angiogenic agent are illustrated in Auerbach and Auerbach, Pharmacol. Ther., 63: 265-311 (1994); O'Reilly, Investigational New Drugs, 15: 5-13 (1997); J. Nat'l Cancer Instit., 88: 786-788 (1996); and U.S. Pat. Nos. 5,593,990; 5,629,327 and 5,712,291. In another embodiment, the anti-neoplasm agent used is an alkylating agent, an antimetabolite, a natural product, a platinum coordination complex, an anthracenedione, a substituted urea, a methylhydrazine derivative, an adrenocortical suppressant, a hormone, and an antagonist.

Other anti-neoplasm agents include, but are not limited to, cytidine, arabinosyladenine (araC), daunomycin, doxorubicin, methotrexate (MTX), fluorinated pyrimidines such as 5-fluorouracil (5-FU), hydroxyurea, 6-mercaptopurine, plant alkaloids such as vincristine (VCR), VP-16 and vinblastine (VLB), alkylating agent, cisplatin, nitrogen Mustard, trisamine, procarbazine, bleomycin, mitomycin C, actinomycin D, or an enzyme such as L-Asparaginase. The anti-neoplasm agent can also be an oncogene inhibitor such as an anti-oncogene antibody or an anti-oncogene antisense oligonucleotide. In another embodiment, the anti-neoplastic agent is a cellular matrix inhibitor such as an anti-cellular-matrix antibody or an anti-cellular-matrix antisense oligonucleotide. For example, antibodies and antisense oligonucleotides against caveolin-1, decorin, cadherins, catenins, integrins, and other cellular matrix or cellular matrix genes can be used.

In a specific embodiment, the combination further comprises a tumor suppressor gene for combined intratumoral therapy and gene therapy. The gene can be used in the form of naked DNA, complexed DNA, cDNA, plasmid DNA, RNA or other mixtures thereof as components of the gene delivery system. In another embodiment, the tumor suppressor gene is included in a viral vector. Any viral vectors that are suitable for gene therapy can used in the combination. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and vaccinia virus vectors can be used. In addition, the genes can be delivered in a non-viral vector system such as a liposome wherein the lipid protects the DNA or other biomaterials from oxidation during the coagulation.

D. Methods and Kits for Prognosing or Diagnosing a Disease or Disorder Associated with Slit2 Mediated Angiogenesis In yet another aspect, the present invention is directed to a method for prognosing or diagnosing a disease or disorder associated with Slit2 mediated angiogenesis in a subject, which method comprises: a) obtaining a test sample from a test subject and assessing Slit2 and/or Slit2 receptor level in said test sample; b) obtaining a control sample from a control subject not having a disease or disorder associated with Slit2 mediated angiogenesis and assessing Slit2 and/or Slit2 receptor level in said control sample; and c) comparing Slit2 and/or Slit2 receptor levels assessed in a) and b), whereby an elevated Slit2 and/or Slit2 receptor level in said test subject relative to Slit2 and/or Slit2 receptor level in said control subject indicates that said test subject has said disease or disorder associated with Slit2 mediated angiogenesis. Preferably, the Slit2 receptor is Robo1 or Robo4. The Slit2 and/or Slit2 receptor level can be assessed at suitable level, e.g., at nucleic acid or protein level.

In yet another aspect, the present invention is directed to a kit for prognosing or diagnosing a disease or disorder associated with Slit2 mediated angiogenesis in a subject, which kit comprises: a) a means for obtaining a test sample from a test subject and a control sample from a control subject; b) a means for assessing Slit2 and/or Slit2 receptor level in said test and control samples; and c) a means for comparing Slit2 and/or Slit2 receptor levels assessed in said test and control samples. Preferably, the Slit2 receptor is Robo1 or Robo4.

E. Examples

Angiogenesis is a cellular process of capillary sprouting and configuring of neovasculatures from the existing blood vessels. It plays essential roles in the pathogeneses of ischemia and hypoxia, atherosclerosis, leukocyte trafficking and recruitment, hemostasis, wound healing, vascular leaky syndrome, diabetic retinopathy, macular degeneration, neovascular glaucoma, psoriasis, rheumatoid arthritis, hemangioma, and cancer growth and metastasis. Slit2, a protein expressed on midline cells and endothelial cells, reacts with a cell surface transmembrane protein, Roundabout1 (Robo1), and functions as a repellent for axon guidance and branching, neuronal migration, and as an endogenous inhibitor for leukocyte chemotaxis. Here we found the expressions of Slit2, in a centrical gradient, on human cancers and Robo1 on tumor endothelial cells. Recombinant Slit2 protein attracted the migration and promoted the tube formation of endothelial cells in a Robo1-dependent manner. Specific neutralization of this interaction markedly reduced the tumor blood vessels and the masses of human A375 cell malignant melanoma in vivo. These findings indicate a model of the crosstalk between cancer cells and vascular endothelial cells for their blood supplies and implicate an intervention targeted at the Slit2 mediated angiogenesis for diagnosis, treatment and prevention of the above disorders.

Expressions of Slit2 in A375 Cells and Robo1 in Endothelial Cells

Using semi-quantitative reverse-transcription coupled to the polymerase chain reaction (RT-PCR), we found that A375 cells, a cell line derived from a human malignant melanoma, expressed Slit2 mRNA and human umbilical vein endothelial cells (HUVECs) expressed Robo1 mRNA, respectively (FIGS. 1a and e). The expressions of Slit2 mRNA in A375 cells and Robo1 mRNA in HUVECs were confirmed by Northern blotting with the $^{32}$P-labeled Slit2 and Robo1 cDNA fragments (FIGS. 1b and f). The expressions of Slit2 protein in A375 cells (FIG. 1c) and tumor solids from A375 cells (FIGS. 1h and i) and Robo1 protein in HUVECs (FIG. 1g) and tumor endothelial cells (FIG. 1i) were detected by immunoblotting and immunohistochemical staining with anti-Slit2 and anti-Robo1 Abs, but not with preimmune IgG (FIGS. 1c, g, h and i). In consistent with the previous reports, Slit2 was found to be localized on the cell surfaces (FIGS. 1h and i). Likewise, we found that the majority of Slit2 was associated with A375 cells in the cell culture conditions, even though a small amount of Slit2 in the supernatants was also detected (data not shown). Notably, there appeared to have a Slit2 gradient on the tumor-solids, with the lower staining density in the periphery and the higher staining density in the center (FIG. 1h). The in situ expressions of Slit2 on malignant melanomas and Robo1 on tumor endothelial cells thus suggest a possible paracrine Slit2/Robo1 interaction in the pathogenesis of cancers.

The Slit2-Induced Migrations and Tube Formations

As several "neurological" migratory cues can induce angiogenesis, it is intriguing to investigate whether Slit2 has an angiogenic activity. During the angiogenic process, vascular endothelial cells undergo migration, differentiation and proliferation. We first investigated whether Slit2 had any chemotactic effects on the migration of HUVECs using Boyden chamber assay. As expected, the purified recombinant human Slit2 (FIG. 1d) in the lower chambers, like bFGF (basic fibroblast growth factor), induced the migration of HUVECs in a dose-dependent manner (FIG. 2a). Preincubation of Slit2 with RoboN (an extracellular fragment of Robo1 Li H. S. et al. Cell 96:807-818 (1999); Wu, W. et al. Nature 400:331-336 (1999)) or preincubation of HUVECs with R5 (an $IgG_{2b}$ monoclonal antibody to the first IgG domain of Robo1; FIG. 4g) significantly neutralized the Slit2-induced migration; however, RoboN or R5 did not affect the bFGF-induced migration of HUVECs (FIGS. 2a and b). These results indicate that Slit2 can mediate the migration of HUVECs.

To determine the functional significance of Robo1, we performed the reconstitution experiments using Robo1/293 cells (Li, H. S. et al. Cell 96:807-818 (1999)). Remarkably, Slit2 and bFGF both promoted the migration of Robo1/293 cells, but RoboN only neutralized Slit2-induced, but not the bFGF-induced, migration of Robo1/293 cells (FIG. 2c). Further, bFGF, but not Slit2, triggered the migration of V/293 cells. Evidently, Robo1 is essential for the Slit2-induced cell migrations.

To corroborate the above findings, we carried out the experiments in which a gradient of Slit2 or bFGF was generated to monitor the directional migration of HUVECs. Indeed, HUVECs migrated toward to a higher concentration of Slit2, attesting to the attractive directionality for the Slit2-induced migration of endothelial cells (FIGS. 2d, e and f). bFGF induced the migration of HUVECs; however, this migration was not directional (FIGS. 2d, e and f). RoboN added in the bath neutralized the Slit2-induced directional migration, but had no inhibitory effects on the bFGF-induced migration (FIGS. 2e and f). These data indicate that Slit2 can attract the directional migration of vascular endothelial cells by its interaction with Robo1. This is in sharp contrast to the repulsive effect of Slit2 on neurons and to the non-directional or random migratory effect of bFGF on HUVECs.

We then examined whether Slit2 could induce the tube formation of HUVECs. Indeed, Slit2 facilitated the tube formation of HUVECs in a dose-dependent manner (FIGS. 2g and h). bFGF also promoted tubulogenesis. Preincubation of Slit2 with RoboN or preincubation of HUVECs with R5 neutralized the effect of Slit2, resulting in the less and shorter tubular structures (FIGS. 2h and i). Our results thus indicate that Slit2 has an angiogenic activity in vitro. It should be mentioned that Slit2 had no detectable activity on the proliferation of HUVECs (data not shown).

The Inhibition of Tumor Angiogenesis and Growths of Malignant Melanoma

As A375 cells expressed Slit2 and Slit2 induced the migration and tube formation of endothelial cells in vitro, it was impetus to us to evaluate the pathological significance of the Slit2/Robo1 interaction in tumor angiogenesis in an animal model. To specifically neutralize this interaction in vivo, three single cell clones stably expressing RoboN (RoboN/A375_C1, C2 and C3 cells) and one cell clone stably expressing the plain vector (V/A375 cells) were established. They were characterized by immunoblotting for RoboN and Slit2 expressions (FIG. 3a) and tested for their in vitro growth rates to ensure that they all grew at the similar rates in the cell culture conditions (FIG. 3b).

They were then inoculated subcutaneously into athymic nude mice. When compared to those from V/A375 cells, tumor solids from RoboN/A375_C1, C2 and C3 cells had the significant reductions of vessel densities (FIGS. 3c and d). Consequently, tumors from Robo1/A375_C1, C2 and C3 cells all grew markedly slower (FIG. 3e). As an alternative approach, we tested R5, an $IgG_{2b}$ blocking monoclonal antibody against Robo1, and found that it also clearly reduced the tumor vessels and masses (FIGS. 3g-k). These in vivo results demonstrate the biological importance of the Slit2/Robo1 interaction in the angiogenesis and the growth of human malignant melanoma.

As endothelial cells expressed both Slit2 and Robo1 and Slit2 inhibited the leukocyte chemotaxis, we measured the leukocyte counts in the bloods and in the tumor solids. We found no clear differences among these groups (FIGS. 3f and l). The amounts of leukocytes within the tumor solids were confirmed by the H&E staining of the tissue sections (data not shown). These data apparently argued against the critical involvements of the leukocytes mediated by Slit2 in the pathogenesis of malignant melanoma. The very faint staining of Slit2 on the tumor endothelial cells (FIGS. 1i and 4c) also argued against the essential roles of a potential autocrine Slit2/Robo1 interaction during the development of tumor solids.

The Expression of Slit2 in Human Cancers

To explore the implications of our findings, we went on to examine whether human cancer cell lines originated from different tissues and organs expressed Slit2. Slit2 was indeed expressed in A375 cells (malignant melanoma), SCaBER cells (bladder squamous carcinoma), SK-N-SH cells (neuroblastoma), NCI-H446 cells (small cell lung cancer), LoVo cells (colon adenocarcinoma), T24 cells (bladder transitional cell carcinoma), ZR-75-30 cells (breast cancer), Acc-2 and Acc-M cells (adenoid cystic carcinoma of salivary gland), SMMC-7721 cells (hepatocellular carcinoma) and A673 cells (rhabdomyosarcoma; FIG. 4a). But Slit2 was apparently absent in A549 cells (lung cancer), HeLa cells (cervical epithelial adenocarcinoma), MCF-7 cells (breast adenocarcinoma) and 786-O cells (primary renal cell adenocarcinoma). Whether HCT-8 cells (ileocecal colorectal adenocarcinoma; one major band at ~130 kDa) and CNE cells (nasopharyngeal cancer; one major band at ~130 kDa and one minor band at ~100 kDa) expressed Slit2, which might partially degraded, remained to be further determined.

The finding of Slit2 expression in a variety of cancer cell lines is consistent with the recent report of Slit2 expression in prostate cancers using a RT-PCR-based approach. Along this line of the investigation, we examined human malignant melanoma, rectal mucinous adenocarcinoma, breast invasive carcinoma, hepatocellular carcinoma and found that they all expressed Slit2 (FIG. 4b). Notably, within the sections of breast carcinoma, there apparently had more Slit2 staining on the spots where more cancer cells and blood vessels existed (FIG. 4c). In contrast, there had less Slit2 staining on the locations where fewer cancer cells and blood vessels were present. Similar manifestations were observed for human hepatocellular carcinoma, but they were not obvious for malignant melanoma and rectal mucinous adenocarcinoma (data not shown). These direct correlations apparently implicate the functional significance for the Slit2 induced tumor angiogenesis in the pathogenesis of various human cancers.

In conclusion, our findings indicate a model of crosstalk between cancer cells and vascular endothelial cells for the blood supply of cancers. The facts that the abrogation of this Slit2/Robo 1 interaction can attenuate the vessel formation and, consequently, the cancer growth have demonstrated the functional importance of this molecular pair for the blood supply of malignant melanoma. As the majority of cancer cells originated from different tissues and organs and various human cancers express Slit2, we believe that the pathological significance for the Slit2/Robo1 interaction in tumor angiogenesis deserves further studies.

Methods of RT-PCR and Northern Blotting

Primary HUVECs were cultured as previously described (Geng, J.-G. et al. Nature 343:757-760 (1990)). Semi-quantitative RT-PCR was performed as before (Ma, Y.-Q. and Geng, J.-G. J. Immunol. 165:558-565 (2000)). Primers used were human Robo1 sense (+4440) 5'-CCT ACA CAG ATG ATC TTC C-3' (SEQ ID NO: 1) and antisense (−4956) 5'-CAG AGG AGC CTG CAG CTC AGC TTT CAG TTT CCT C-3' (SEQ ID NO: 2); human Slit2 sense (+3611) 5'-GGT GAC GGA TCC CAT ATC GCG GTA GAA CTC-3' (SEQ ID NO: 3) and antisense (−4574) 5'-GGA CAC CTC GAG CGT ACA GCC GCA CTT CAC-3' (SEQ ID NO: 4); human βactin sense (+1) 5'-ATG GAT GAT GAT ATC GCC GC-3' (SEQ ID NO: 5) and antisense (−1127) 5'-CTA GAA GCA TTT GCG GTG G-3' (SEQ ID NO: 6). Total RNAs from A375 cells and the primary culture of HUVECs were also probed with the $^{32}$P-labeled Slit2 or Robo1 cDNA fragments.

Methods of Antibody Generation, Immunoblotting and Immunostaining

Slit2-GST (encoding 57-207 amino acids of human Slit2 cDNA) and Robo1-GST fusion proteins (encoding either 1-168 or 961-1217 amino acids of rat Robo1 cDNA) were constructed into a pGEX-4T-1 vector (Amersham Pharmacia Biotech). The purified fusion proteins were used as the antigens to immunize rabbits and mice for generation of anti-Slit2 and anti-Robo1 polyclonal and monoclonal antibodies. The equal amounts of cell lysates were used for immunoblotting. Immunohistochemical examinations were performed as described before (Liu, L.-P. et al. Biochem. Biophys. Res. Commun. 286:281-291 (2001)).

Methods of Isolation of Slit2 and RoboN

A stable human embryonic kidney 293 cell line secreting full-length human Slit2 with a myc tag at its carboxyl terminus (Slit2/293 cells) was established as previously described (Li, H. S. et al. Cell 96:807-818 (1999); Wang, K.-H. et al. Cell 96:771-784 (1999)). The highly purified Slit2 protein was obtained from the conditioned medium by affinity chromatography using 9E10 mAb to the myc tag (~1 mg ml$^{-1}$ of Affi-Gel 10; Bio-Rad). The silver staining and immunoblotting of the purified Slit2 was carried out as described (Ma, L. et al. J. Biol. Chem. 269:27739-27746 (1994)).

A stable 293 cell line over-expressing the extracellular portion of Robo1 with a hemoagglutinin tag at its carboxyl terminus (RoboN) was established as before (Li, H. S. et al. Cell 96:807-818 (1999); Whitford, K. L. et al. Neuron 33:47-61 (2002)). Affinity beads coupled with a mAb to hemoagglutinin, HA11 (BAbCO), were used to purify RoboN from the conditioned medium as above.

Methods of Boyden Chamber Assay

The cell migration assay was conducted in a 48-well microchemotaxis chamber (Neuro Probe, Inc.) (Terranova, V. P. et al. J. Cell. Biol. 101:2330-2334 (1985)). PVP-free polycarbonate membranes (8 μm pores) were coated with 1% gelatin. The bottom chambers were loaded with or without Slit2 or bFGF (Sigma), while the upper chambers was seeded with HUVECs, Robo1/293 cells or V/293 cells (all at 5×10$^5$ cells ml$^{-1}$) resuspended in M199 medium supplemented with 1% heat inactivated fetal calf serum (FCS). They were incubated at 37° C. for 4 h. The filters were then fixed, stained with 0.5% crystal violet and the cells migrated through the filters were counted.

Methods of Directional Migration Assay

The microscopic gradients of proteins were produced as described (Höpker, V. H. et al. Nature 401:69-73 (1999)). Briefly, a repetitive pressure injection of picoliter volumes of 0.15 μM Slit2 or 1 μM bFGF was applied through a micropipette with a tip at the opening of ~1 μm. The 24-well culture plate was coated with a thin layer of Matrigel (Becton Dickinson Labware) and the testing cells were allowed to settle down and to loosely attach to the Matrigel. The experiments were carried out at 37° C. in the presence of 5% $CO_2$. The pipette tip was placed 100 μm away from the centre of any given cell under testing. Microscopic images were recorded with a CCD camera (JVC) attached to a phase contrast microscope (Olympus IX70) and stored in a computer for the detailed analysis using NIH Image. The migration distances of HUVECs at 2 h were analyzed.

Methods of Tube Formation Assay

The 96-well cell culture plates were coated with 100 μl/well of Matrigel and incubated at 37° C. for 30 min to promote gelling (Malinda, K. M. et al. Identification of laminin α1 and β1 chain peptides active for endothelial cell adhesion, tube formation and aortic sprouting. FASEB J. 13:53-62 (1999)). HUVECs (passages 2 to 3) were resuspended at 1.3×10$^5$ cells per well in M199 medium supplemented with 2% heat inactivated fetal calf serum. Aliquots of cells (0.1 ml per aliquot) were added to each Matrigel-containing well. The tubular structures were recorded and photographed at 12 to 18 h.

Methods of Xenografted Tumor Growth Model

A375 cells were transfected using (Gibco) LIPOFECTIN and selected by 400 μml$^{-1}$ hygromycin B (Sigma). RoboN/A375_C1, C2 and C3 cells as well as V/A375 cells were verified by immunoblotting with the antibodies against Robo1, Slit2 and tubulin (as the loading control). They were resuspended in an aliquot of 0.2 ml DME medium and injected subcutaneously into athymic nude mice (O'Reilly, M. S. et al. Endostatin: An endogenous inhibitor of angiogenesis and tumor growth. Cell 88:277-285 (1997)). For antibody inhibition experiments, mice bearing A375 cell tumors were treated with intraperitoneal injections of R5 or control IgG$_{2b}$ twice per week (1 mg per injection) (Müller, A. et al. Nature 410:50-56 (2001)). Mice were sacrificed 30-35 days later. Mouse bloods were collected before sacrifice for leukocyte counts, and myeloperoxidase activities for measurements of neutrophils within tumor solids were performed as before (Wang, J.-G. et al. Inflamm. Res. 51:435-43 (2002)).

Methods of Cell Proliferation Assay

All transfectants were grown in exponential phases and detached by trypsin treatment. Viable cells (5×10$^3$ cells ml$^{-1}$) were plated into 96-well tissue culture plates in 100 μl complete medium and cultured at 37° C. in 5% $CO_2$ atmosphere. At different time points, tetrazolium salt was added (20 μl per well) and incubated at 37° C. for 4 h. The insoluble blue formazan product was solubilized by addition of 100 μl/well 10% SDS/5% isobutanol. The plates were read on a microtiter plate reader using a test wavelength of 570 nm and a reference wavelength of 630 nm.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A method for treating cancer associated with Slit2 mediated tumor angiogenesis in a subject, which method comprises:

administering a compound effective to reduce or prevent Slit2-Slit2 receptor protein-protein interaction to the subject at a level sufficient to treat the cancer associated with Slit2 mediated tumor angiogenesis in said subject, wherein the cancer is a solid tumor cancer that comprises cells expressing Slit2, and wherein the solid tumor cancer is adenoid cystic carcinoma of salivary gland or hepatocellular carcinoma; and wherein the compound that reduces or prevents Slit2-Slit2 receptor protein-protein interaction is selected from the group consisting of an anti-Slit2 antibody, an anti-Slit2 receptor antibody and a Slit2 receptor fragment derived from extracellular domain of the Slit2 receptor that is capable of binding to Slit2.

2. The method of claim 1, wherein the anti-Slit2 antibody or anti-Slit2 receptor antibody is selected from the group consisting of a polyclonal antibody, a monoclonal antibody, a Fab fragment and a F(ab')$_2$ fragment.

3. The method of claim 1, wherein the Slit2 receptor is Robo1 or Robo4.

4. The method of claim 3, wherein the anti-Slit2 receptor antibody is an antibody against a first immunoglobulin domain of Robo1.

5. The method of claim 3, wherein the Slit2 receptor fragment is RoboN.

6. The method of claim 1, wherein the compound is administered with a pharmaceutically acceptable carrier or excipient.

7. The method of claim 1, wherein the cancer is metastatic.

8. The method of claim 1, wherein the subject is a mammal.

9. The method of claim 8, wherein the mammal is a human.

10. The method of claim 1, wherein the subject is a human and the compound to be administered to the human is a humanized monoclonal antibody.

* * * * *

UNITED STATES PATENT AND TRADEMARK OFFICE
CERTIFICATE OF CORRECTION

PATENT NO. : 7,939,497 B2  
APPLICATION NO. : 10/386386  
DATED : May 10, 2011  
INVENTOR(S) : Geng et al.

Page 1 of 1

It is certified that error appears in the above-identified patent and that said Letters Patent is hereby corrected as shown below:

Title Page, Item (12) "Geng" should read -- Geng, et al. --.

Title Page, Item (75) Inventor is corrected to read:
-- Jian-Guo Geng, Portage (MI);
Biao Wang, Shanghai (CN);
Yang Xiao, Shanghai (CN);
Beibei Ding, Shanghai (CN);
Na Zhang, Shanghai (CN) --.

Signed and Sealed this
Twenty-fourth Day of November, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Human Robo 1 sense primer

<400> SEQUENCE: 1
cctacacaga tgatcttcc                                              19

<210> SEQ ID NO 2
<211> LENGTH: 34
<212> TYPE: DNA
<213> ORGANISM: Artificial Sequence
<220> FEATURE:
<223> OTHER INFORMATION: Human Robo 1 antisense primer

<400> SEQUENCE: 2
cagaggagcc tgcagctcag ctttcagttt cctc                             34

<210> SEQ ID NO 3
<211> LENGTH: 30
<212> TYPE: DNA
<213> ORGANISM: Artificial Sequence
<220> FEATURE:
<223> OTHER INFORMATION: Human Slit2 sense primer

<400> SEQUENCE: 3
ggtgacggat cccatatcgc ggtagaactc                                  30

<210> SEQ ID NO 4
<211> LENGTH: 30
<212> TYPE: DNA
<213> ORGANISM: Artificial Sequence
<220> FEATURE:
<223> OTHER INFORMATION: Human Slit2 antisense primer

<400> SEQUENCE: 4
ggacacctcg agcgtacagc cgcacttcac                                  30

<210> SEQ ID NO 5
<211> LENGTH: 20
<212> TYPE: DNA
<213> ORGANISM: Artificial Sequence
<220> FEATURE:
<223> OTHER INFORMATION: Human beta-actin sense primer

<400> SEQUENCE: 5
atggatgatg atatcgccgc                                             20

<210> SEQ ID NO 6
<211> LENGTH: 19
<212> TYPE: DNA
<213> ORGANISM: Artificial Sequence
<220> FEATURE:
<223> OTHER INFORMATION: Human beta-actin antisense primer

<400> SEQUENCE: 6
ctagaagcat ttgcggtgg                                              19